United States Patent [19]

Chan

[11] 4,144,261
[45] Mar. 13, 1979

[54] PROCESS FOR PREPARING ORGANOTHIO-ALDOXIME COMPOUNDS

[75] Inventor: John K. Chan, Charleston, W. Va.

[73] Assignee: Union Carbide Corporation, New York, N.Y.

[21] Appl. No.: 831,072

[22] Filed: Sep. 7, 1977

[51] Int. Cl.$^2$ ............................................. C07C 131/00
[52] U.S. Cl. ........................ 260/453 RW; 260/566 A
[58] Field of Search ................... 260/566 A, 453 RW

[56] References Cited

U.S. PATENT DOCUMENTS

| | | | |
|---|---|---|---|
| 3,535,361 | 10/1970 | Anders et al. | 260/566 A |
| 3,574,736 | 4/1971 | Fuchs | 260/566 A |
| 3,658,869 | 4/1972 | Soloway et al. | 260/453 RW |
| 3,752,841 | 8/1973 | Fuchs | 260/453 RW |
| 3,873,624 | 3/1975 | Mathew et al. | 260/566 A |

*Primary Examiner*—Gerald A. Schwartz
*Attorney, Agent, or Firm*—Robert C. Brown

[57] ABSTRACT

An improved process for preparing 1-organothio-aldoxime compounds by chlorinating the corresponding aldoxime and reacting the resulting 1-haloaldoxime with the sodium salt of a mercaptan, said process being conducted in an aqueous solvent containing from 5 to 75 percent by weight of a linear or cyclic polyhydric alcohol having from 2 to 20 carbon atoms.

8 Claims, No Drawings

PROCESS FOR PREPARING ORGANOTHIO-ALDOXIME COMPOUNDS

BACKGROUND OF THE INVENTION

This invention relates to an improved process for preparing 1-organothio-aldoxime compounds. More particularly, this invention is directed to a method of preparing 1-organothio-aldoxime compounds by halogenating the aldoxime in an aqueous sovlent containing from 5 to 75 percent by weight of a linear or cyclic polyhydric alcohol containing two or more hydroxyls and having from 2 to 20 carbon atoms, and reacting the resulting 1-haloaldoxime with the sodium salt of a mercaptan.

1-Organothio-aldoxime compounds and their preparation by the chlorination of an aldoxime followed by reaction with a sodium mercaptide are well known. U.S. Pat. Nos. 3,658,869 and 3,535,361 disclose a two-step preparation of organothio-aldoxime compounds by chlorination of an aldoxime in aqueous medium followed by reaction of the resultant chloroacetaldoxime with a thiol. The main drawback of such prior art processes is low yield of the desired product. U.S. Pat. No. 3,752,841 discloses an improvement of the basic process in which the reaction medium is dimethylformamide or an aqueous mixture containing at least ten weight percent dimethylformamide. This process also suffers from a number of inherent disadvantages. The separation problems of the 1-hydrocarbylthioaldoxime compounds are complicated by the use of the dimethylformamide since these compounds are very soluble in dimethylformamide. This makes it necessary to use costly, elaborate and cumbersome purification procedures, such as distillation, solvent extraction and the like, to isolate the final product.

It is, therefore, the object of this invention to provide a more effective process for preparing 1-organothioaldoxime compounds in exhanced yields.

SUMMARY OF THE INVENTION

According to the present invention there is provided an improved process for preparing a compound of the formula:

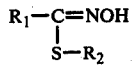

wherein:

$R_1$ and $R_2$ are individually alkyl, alkoxyalkyl, cycloalkyl, phenyl or phenylalkyl, all of which may be either unsubstituted or substituted with one or more halo, cyano, nitro or dialkylamino substituents, in which an aldoxime of the formula $R_1CH=NOH$ is reacted with a halogen to form the corresponding 1-haloaldoxime and said 1-haloaldoxime is reacted with the sodium mercaptide salt of a compound of the formula $R_2SH$, the improvement which comprises conducting the reaction in an aqueous solution containing from about 5 to about 75 percent of a linear or cyclic polyhydric alcohol having from 2 to 20 carbon atoms.

DESCRIPTION OF THE PREFERRED EMBODIMENT

The halogenation step to form the 1-haloaldoxime reactant is conveniently performed by reacting the halogen and the aldoxime in an aqueous reaction medium containing from 5 to 75 weight percent of a linear or cyclic polyhydric alcohol. The formation of by-products is minimized by this process and the resulting products can be purified without resorting to elaborate and costly purification techniques.

Useful polyhydric alcohols are those having from 2 to 20 carbon atoms. Illustrative of useful polyhydric alcohols are ethylene glycol, glycerol, erythritol, arabitol, sorbitol and the like. The concentration of polyhydric alcohols in the reaction solvent may vary from about 5 to about 75 percent by weight, based on the total weight of water employed. Preferred polyhydric alcohol concentrations are from about 10 to 50 percent by weight.

In general aldoxime reactants that are useful in the conduct of the process of this invention are well known to those skilled in the art. The aldoxime may be either an unsubstituted or substituted alkyl, cycloalkyl, alkoxyalkyl aryl or aralkyl compound. Illustrative of aldoxime reactants are alkanaldoximes such as acetaldoxime, propionaldoxime, isobutyraldoxime, n-valeraldoxime and the like. Also useful are the cyclic aldoximes and aromatic aldoximes, i.e. those compounds in which R is cyclic groups such as cyclohexane, cyclopentane, cycloheptane alkoxyalkyl groups such as methoxymethyl, ethoxymethyl, proproxymethyl or aromatic groups such as benzene, p-methylbenzene, p-ethylbenzene, benzyl, phenethyl and the like. As previously noted these radicals may be suitable substituted with non-reactive functional groups, re, cyano, halo, nitro or alkyl groups.

The quantity of aldoxime employed in from about 5 to about 75 percent by weight based on the total weight of the solvent. The preferred amount is from about 10 to about 25 weight percent. Greater amounts of solvent can of course be used, except such amounts merely dilute the components in the reaction mass with no particular advantage being obtained.

The aldoxime compounds utilized as reactants in the process of this invention can be conveniently prepared according to conventional methods. For example, these compounds can be conveniently prepared by reacting an appropriate aldehyde with hydroxylamine salts, optionally in the presence of an alkali metal hydroxide or carbonate. Another method involves reacting the corresponding aldehyde in a water medium with sodium nitrite, sodium bisulfite and sulfur dioxide.

In general, the aldoxime reactant will be reacted with a stoichiometric quantity of the halogen; however, an excess or less than stoichiometric amounts of the halogen may also be employed. In the preferred embodiments of this invention the quantity of halogen may vary from the stoichiometric amount by from plus or minus one percent.

The 1-haloalkoxime intermediate of the halogenation step may be isolated and purified for use at some later time or it may be reacted with the mercaptide salt without purification or isolation. If the 1-haloaldoxime intermediate is employed in an in situ process, i.e. without isolation and/or purification, the stoichiometric amount of by-product hydrogen chloride must be neutralized at some later point during the reaction.

The mercaptide salts utilized as reactants in the process of this invention as well as their method of preparation are well known to those skilled in the synthetic arts. The mercaptide salt reactant can be conveniently prepared by treating the corresponding mercaptan with an inorganic base.

The base employed should be of sufficient basicity and quantity to form a salt of the mercaptan. In addition an additional quantity of base may be added at the juncture in an amount sufficiently to neutralize the halogen halide produced in the second step of the process. The additional quantity of base may also be added after the addition of mercaptide salt to the reaction mixture.

Useful mercaptan (thiols) include the alkyl mercaptans such as methyl mercaptan, ethyl mercaptan, propyl mercaptan, isopropyl mercaptan, hexyl mercaptan, isobutyl mercaptan, pentyl mercaptan, decyl mercaptan and the like. Other useful mercaptans are those in which $R_2$ is a cyclic group such as cycloheptane, cyclohexane, cyclopentane, cyclobutane or the like; those in which $R_2$ is an alkoxyalkyl group such as methoxymethyl, propoxymethyl, methoxyethyl or the like; or those in which $R_2$ is an aromatic group such as benzene, 2-methylbenzene, 3-alkyoxybenzene, benzyl, phenethyl and the like. As previously noted these radicals may be suitably substituted with non-reactive functional groups such as halogen, cyano, alkyl, nitro, etc.

Suitable organic bases include the alkali metal alkoxides such as sodium methoxide, sodium ethoxide and the like.

Useful inorganic bases include the alkali metal and the alkaline earth metal carbonates such as lithium, sodium, potassium, calcium and barium carbonate; the alkali metal bicarbonates such as sodium, bicarbonate, potassium, bicarbonate and the like; the alkali metal hydroxides such as lithium hydroxide, sodium hydroxide, potassium hydroxide and the like. Inorganic bases are preferred for use in the process of this invention.

The mercaptide salt reactant may be generated outside the presence of the aldoxime reactant and used at some latter date. Alternatively, the mercaptide salt reactant may be generated in-situ, i.e. in presence of the aldoxime reactant.

In general, the 1-haloaldoxime reactant is reacted with a stoichiometric quantity of the mercaptide salt, although, it should be understood that the quantity of mercaptide salt employed can vary from stoichiometric to as much as a 50 percent excess. In the preferred embodiments of this reaction the quantity of mercaptide salt employed will vary from stoichiometric to plus 10 percent.

The reaction temperature for the halogenation and the mercaptide addition steps is not critical and can be varied over a wide range. The reactions can be conducted at a temperature in the range of from about $-20°$ C. and upwards to approximately $40°$ C. Preferred reaction temperatures are from about $-10°$ C. to about $15°$ C. with particularly preferred reaction temperatures being from about $0°$ C. to about $-10°$ C. At temperatures below $-20°$ C. the rate of reaction becomes markedly slower, while at temperatures above $40°$ C. product degradation and side reaction may occur.

Reaction pressures are not critical. The process of this invention can be conducted at either subatmospheric, atmospheric or superatmospheric pressures. For convenience, the reaction is usually conducted at atmospheric or autogenous pressure.

The process of this invention is carried out over a period of time sufficient to produce the desired 1-organoaldoxime compound in adequate yield. In general, residence times can vary from about a few minutes to 24 hours or longer. In most instances, when employing preferred reaction conditions, reaction times will be found to vary from about 2 hours to about 3 hours. Reaction time is influenced to a significant degree by the reactants; the reaction temperature; the concentration and choice of base; the choice and concentration of reaction solvent and by other factors known to those skilled in the art.

The process of this invention can be conducted in a batch, semicontinuous or continuous fashion. The reaction can be conducted in a single reaction zone or in a plurality of reaction zones, in series or in parallel or it may be conducted intermittently or continuously in an elongated tubular zone or series of such zones. The materials of construction employed should be inert to the reactants during the reaction and the fabrication of the equipment should be able to withstand the reaction temperatures and pressure.

The reaction zone can be fitted with one or more internal and/or external heat exchanger(s) in order to control undue temperature fluctuations, or to prevent any possible "runaway" reaction temperatures. In preferred embodiments of the process, agitation means to vary the degree of mixing the reactions mixture can be employed. Mixing by vibration, shaking, stirring, rotation, oscillation, ultrasonic vibration or the like are all illustrative of the type of agitation means contemplated. Such means are available and well known to those skilled in the art.

The reactants and reagents may be initially introduced into the reaction zone batchwise or it may be continuously or intermittently introduced in such zone during the course of the process. Means to introduce and/or adjust the quantity of reactants introduced, either intermittently or continuously into the reaction zone during the course of the reaction can be conveniently utilized in the process especially to maintain the desired molar ratio of the reaction solvent, reactants and reagents.

EXAMPLE I

Procedure: Acetaldoxime (30 g., 0.5 mole) was dissolved in 200 g. of a solvent mixture containing 175 g. of water and 25 g. of ethylene glycol, and the solution was cooled to $-5°$ to $-10°$ C. Over a period of 20–30 minutes, 30 g. of chlorine was introduced to to the solution with good agitation. During chlorination, the reaction temperature was maintained at $-5°$ to $-10°$ C. An additional 6 g. of chlorine was added in 10 minutes. The mixture was stirred for 10–15 minutes at $-10°$ C. A sodium methyl mercaptide solution was prepared by dissolving methyl mercaptan (25 g., 0.52 mole) in a caustic solution containing 40 g. of sodium hydroxide in 100 g. of water. The mercaptide solution was fed directly into the acethydroxamoyl chloride solution at $-10°$ C. over a 15–20 minute period. The reaction mixture was stirred for an additional 15 minutes and then neutralized to pH 7.5 with a 50-percent caustic solution. The crystalline methyl hydroxythioacetimidate was recovered at $-10°$ C. by filtration. The methyl hydroxythioacetimidate was reslurred in hexane, filtered and dried to obtain 47 gram of methylhydroxythioacetimidate mp $87°–89°$ C. This represented a 90% yield.

EXAMPLE II

Procedure: Hydroxylamine hydrochloride (35 g., 0.5 mole) was dissolved in an aqueous mixture consisting of 140 g. of water and 25 g. of ethylene glycol. The mixture was kept at 10°-20° C. while adding dropwise a solution of acetaldehyde (22 g., 0.5 mole) in 22 g. of water and a caustic solution containing 20 g. of sodium hydroxide (0.5 mole) in 40 g. of water simultaneously. After the addition was completed, the reaction mixture was stirred at 10°-25° C. for one hour longer. The reaction mixture was then cooled to −5° to −10° C. and 36 g. of chlorine was introduced over a period of 30-40 minutes. The reaction mixture was stirred for 15 minutes longer at −10° C. while a sodium methyl mercaptide solution was prepared by dissolving methyl mercaptan (25 g., 0.52 mole) in a caustic solution containing 40 g. of sodium hydroxide in 100 g. of water. The mercaptide solution was fed directly into the acethydroxamoyl chloride solution at −10° C. over a 15-20 minute period. The reaction mixture was stirred for an additional 15 minutes and then neutralized to pH 7.5 with a 50-percent caustic solution. The crystalline methyl hydroxythioacetimidate was recovered at −10° C. by filtration. The wet product, after being sucked as dry as possible on the Buchner funnel, was re-slurried in hexane. Methyl hydroxythioacetimidate, after filtration and drying, was obtained in 82 percent yield based on acrtaldehyde having a melting point of 88°-90° C.

The reactions of Examples III to XV were conducted utilizing the procedure of Example I. In these examples, 0.50 moles of acetaldoxime; 0.50 moles of chlorine; 1.00 moles of sodium hydroxide and 0.52 moles of methyl mercaptan were the reactants, except as noted in TABLE I. The three reaction solvents employed were ethylene glycol (ETG) and water; glycerol (GLC) and water and sorbitol (SBL) and water.

TABLE I

| Ex | Reaction Solvent Wgt. % polyol | Wgt. % $H_2O$ | Reaction Temperature | Reaction b Time (min) | % Yield of Oxime | Melting Point ° C. |
|---|---|---|---|---|---|---|
| III | 75% $ETG^c$ | 25 | −5 to −10 | 70 | 78 | 87-89 |
| IV | 50% $ETG^c$ | 50 | −5 to −10 | 70 | 84 | 85-87 |
| V | 25% $ETG^c$ | 75 | −5 to −10 | 70 | 87 | 87-89 |
| VI | 12% $ETG^c$ | 88 | −5 to −10 | 70 | 90 | 87-89 |
| VII | 5% $ETG^c$ | 95 | −5 to −10 | 70 | 84 | 87-89 |
| VIII | 12% $ETG^c$ | 88 | −2 to +2 | 70 | 86 | 87-89 |
| IX | 12% $ETG^c$ | 88 | 10 | 70 | 77 | 88-89 |
| X | 12% $ETG^c$ | 88 | 20 | 70 | 69 | 88-89 |
| XI | 12% $ETG^c$ | 88 | −2 to +2 | 120 | 81 | 88-89 |
| $XII^a$ | 12% $ETG^c$ | 88 | −5 | 70 | 86 | 86-88 |
| XIII | 25% $SBL^d$ | 75 | −5 to −10 | 70 | 86 | 88-90 |
| XIV | 25% $GCL^e$ | 75 | −5 to −10 | 70 | 90 | 88-90 |
| XV | 43% $SBL^d$ | 57 | −5 to −10 | 70 | 89 | 88-91 |

$^a$.70 moles of methyl mercaptan
$^b$The reaction time is for the chlorination step; the second step required about one hour
$^c$ETG is an abbreviation for ethylene glycol
$^d$SBL is an abbreviation for sorbitol
$^e$GLC is an abbreviation for glycerol To more particularly demonstrate the increased efficiency of the process of this invention in comparison with known processes, the experimental results of representative examples of this invention were compared with the experimental results from two examples of known processes. The comparison data is set forth in TABLE II below. The known processes were conducted using water as the reaction solvent as described in Examples XVI and XVII below:

EXAMPLE XVI

Procedure: Acetaldoxime (30 g., 0.5 mole) was dissolved in 200 g. of water and the solution cooled to −5 to −10° C. Over a period of 20 to 30 minutes, 30 g. of chlorine was introduced into the solution with agitation. During the chlorine addition, the reaction temperature was maintained at −5° to −10° C. An additional 6 grams of chlorine was added in 10 minutes. The mixture was stirred for 10-15 minutes at −10° C. A sodium methyl mercaptide solution was prepared by dissolving methyl mercaptan (25 g, 0.52 mole) in a caustic solution containing 40 g. of sodium hydroxide in 100 g. of water. The mercaptide solution was fed directly into the reaction mixture over a 15 to 20 minute time period while maintaining the temperature at −10° C. The reaction mixture was stirred for an additional 15 minutes and then neutralized to a pH 7.5 by addition of 50% sodium hydroxide solution. Crystaline methyl hydroxythioacetimidate was recovered at −10° C. by filtration. The product was re-slurried in hexane, filtered and dried to obtain 43 grams (83% yield) of methyl hydroxythioacetimidate, mp 87°-88° C.

EXAMPLE XVII

Procedure: Acetaldoxime (30 g., 0.5 moles) was dissolved in 125 g. of water and the solution was cooled to −10° to 0° C. Chlorine (35.5 g., 0.5 mole) was introduced over a period of 15 minutes at a pH of 5-6. The reaction mixture was then added over a period of 10 minutes at −10° C. to an aqueous solution of sodium methyl mercaptide, prepared by adding methyl mercaptan (25 g., 0.52 moles) to sodium hydroxide (15 g., 0.37 mole) in water (250 g.) at 0° C. The solid precipitate was formed and the resulting mixture was highly acidic. The product was filtered, washed with a little ice-water and dried to give 29 g. (56% yield) of crystalline methyl hydroxythioacetamidate, m.p. 91°-93° C.

The data presented in TABLE II hereinabove clearly illustrated the greatly increased efficiency of the peracid oxidation process of this invention in comparison with known processes. For example, the known processes of EXAMPLES XVI and XVII which were conducted without a polyhydric alcohol solvent and yields of 83 and 56 percent respectively. These results are to be contrasted with EXAMPLES I, XIV and XV which employ the process of this invention. Note that the aldoxime product of EXAMPLES I, XIV and XV was produced in an 90, 90% and 88% yield, respectively, and thus, for all practical purposes quantitative. This represents a significant increase in yield of the 2-organothioaldoxime compound.

The aldoxime compounds prepared in accordance with the process of this invention have wide utility and are valuable for a number of useful purposes. Some of the compound prepared in accordance with the process of the inventions are valuable intermediates in the preparation of other compounds that exhibit outstanding insecticidal, nematocidal and miticidal activity. Thus, for example, O-(methylcarbamoyl) thioacetylhydroxamate, an outstanding pesticide, may be conveniently prepared utilizing compounds prepared in accordance with this invention as an intermediate. It should be pointed out, however, that other aldoxime compounds prepared by the process of this invention are not limited to use as intermediates in the preparation of pesticidal compounds, but in addition are extremely useful for other purposes which are known to those skilled in the art.

What is claimed is:

1. In a process for preparing a compound of the formula:

$$R_1-\underset{S-R_2}{C}=NOH$$

wherein:

$R_1$ and $R_2$ are individually alkyl, cycloalkyl, phenyl or phenylalkyl, all of which may be either unsubstituted or substituted with one or more alkyl, halo, alkoxy, cyano, nitro or dialkylamino substituents, in which an aldoxime of the formula:

$$R_1CH=NOH$$

is reacted with a halogen to form the corresponding 1-haloaldoxime and said 1-haloalkoxime is reacted with the mercaptide salt of a compound of the formula:

$$R_2SM$$

The improvement which comprises conducting the reaction in an aqueous solution containing from about 5 to about 75 percent by weight of a polyhydric alcohol selected from the group consisting of ethylene glycol, glycerol, sorbitol, erythritol or arabitol at a temperature of from about −10° C. to about 15° C.

2. A process according to claim 1 wherein said polyhydric alcohol is ethylene glycol, glycerol or sorbitol.

3. A process according to claim 1 wherein said aqueous solution contains from about 10 to about 50 percent by weight of a polyhydric alcohol based on the total weight of water.

4. A process according to claim 1 wherein said aqueous solution contains from about 10 to about 35 percent by weight of said polydric alcohol based on the total weight of water.

5. A process according to claim 1 wherein $R_1$ and $R_2$ are individually cyanoalkyl or nitroalkyl having from one to eight carbon atoms.

6. A process according to claim 1 wherein $R_1$ and $R_2$ are individually methyl, ethyl or propyl.

7. A process according to claim 1 wherein $R_1$ and $R_2$ are methyl.

8. A process according to claim 1 which is carried out at a temperature of from about 0° C. to −10° C.

* * * * *